United States Patent [19]

Robert et al.

[11] 4,138,894
[45] Feb. 13, 1979

[54] TRANSVERSAL ACOUSTIC WAVE OPERATING DEVICE

[75] Inventors: André Robert, Paris; Jean Rouge, Montrouge, both of France

[73] Assignee: L'Electronique Appliquée, Montrouge, France

[21] Appl. No.: 640,321

[22] Filed: Dec. 12, 1975

[30] Foreign Application Priority Data

Dec. 16, 1974 [FR] France .................... 74 41311
Nov. 28, 1975 [FR] France .................... 75 36446

[51] Int. Cl.$^2$ .......................................... G01N 29/00
[52] U.S. Cl. .................................. 73/625; 73/645
[58] Field of Search ............. 73/555, 67, 67.2, 67.5 R, 73/67.6, 67.7, 67.8 R, 67.8 S, 67.9, 71.5 US, 594, 625, 645, 646, 647; 340/1 R, 3 R, 15; 333/1.1

[56] References Cited

U.S. PATENT DOCUMENTS

| | | | |
|---|---|---|---|
| 2,625,035 | 1/1953 | Firestone | 73/67.8 R |
| 2,985,009 | 5/1961 | Henry | 73/67.7 |
| 3,019,636 | 2/1962 | Henry | 73/67.7 |
| 3,251,026 | 5/1966 | May | 333/1.1 |
| 3,352,376 | 11/1967 | Dory | 73/71.5 US |
| 3,524,129 | 8/1970 | Ikrath | 73/67.7 |
| 3,587,297 | 6/1971 | Kammer | 73/67.6 |
| 3,812,709 | 5/1974 | Benson et al. | 73/67.5 R |

OTHER PUBLICATIONS

R. T. Smith, "Stress Induced Anisotropy in Solids the Acousto–Elastic Effect," *Ultrasonics*, Jul.–Sep. 1963, pp. 136–147.

*Primary Examiner*—Stephen A. Kreitman
*Attorney, Agent, or Firm*—Kemon & Estabrook

[57] ABSTRACT

The device comprises an elongated acoustic wave translating isotropic body and a pair of transducers applied over one of the two parallel end faces thereof. Said transducers are arranged with relatively crossed axes of linear transversal polarization. The other end face of the isotrope body is intended to be applied to a sample or a structure made of an acoustically active substance presenting anisotropy, either intrinsic or induced, with respect to acoustical polarization. The length of the isotropic body is such that when the transducers are both simultaneously driven by pulsed high frequency voltages which are modulated in respective phase quadrature by a low frequency oscillation, the two transversal acoustic waves propagated through the body vectorially combine so that the opposite end face of the body is the subject of a constant amplitude acoustic wave which rotates at the speed of the pulsation of the low frequency. When, on the other part, an ellipticised acoustic wave of same high and low frequency components is applied from the acoustical polarized anisotropy sample or structure to the end face of the body deprived of transducers, the transducers on the opposite face receive the components of said ellipticized wave and feed circuits for analysing the said components and deriving therefrom the parameters of ellipticization of the received wave.

11 Claims, 6 Drawing Figures

TRANSVERSAL ACOUSTIC WAVE OPERATING DEVICE

SHORT SUMMARY OF THE INVENTION

The present invention concerns improvements in or relating to transversal acoustic wave operating devices for studies and measures of the ellipticization parameters of departure from the linear polarization of acoustic waves passing through bodies, materials, substances and structures presenting a propagation anisotropy, whether induced from an internal stress or intrinsic to acoustically active substances (in this last case, the studies and measures are relevant to the field of acoustical polarimetry).

French Pat. No. 71 40875 dated Nov. 16, 1971, filed by the same Applicant as the present application, describes a transversal acoustic wave operating device intended for similar purposes and is essentially based on the use of an elongated body made of an acoustically birefringent material having fast and slow axes which are reciprocally orthogonal and both perpendicular to the length of the body from end face to end face thereof. The body is driven by a transversal acoustic wave oriented 45° to the said axes and applied to one end face of the body and an electrical field is applied parallel to the direction of one of the said axes. According to its value, this field controls a relative phase shift between the components of the acoustic wave along the said axes as it travels from end face to end face of the body. An acoustical dephasing member, of the same material as the body, is applied to the end face remote from the end face to which is applied the acoustic wave. Said member presents its fast axis 45° to the fast axis of the body.

For acoustical anistropy or polarimetry studies and measurements, the wave issuing from such as device passes through a "sample" and the wave issuing from the sample is received by an identical device wherein the transducer acts as a receiver and feeds an electronic circuit measuring the phase and intensity of the received wave.

A device according to the said French patent presents objectionable drawbacks for instance, the choice of the material of the body and of the dephasing memeber which is restricted to the group of the acoustical birefringent materials having an anisotropy which can be controlled by electric means; the necessity for this electrical control to use high voltages of the order of 10 to 20 kilovolts in peak value; and the necessity of the dephasing member proper added to the body.

In the U.S. Pat. No. 3,251,026 in the names of John E. MAY jr and John H. ROWEN, entitled "Acoustic System", a system is described wherein an acoustical transmission channel made of a gyromagnetic body having at each of its ends a transmitter transducer and a reception transducer which operate separately at different time periods. This system cannot be used for polarimetry or anisotropy purposes.

It is an object of the invention to provide a new and improved acoustical transversal wave operating device which does not present the drawbacks of the former one.

BRIEF DESCRIPTION OF THE DRAWINGS

For describing the invention in full details, reference is made to the accompanying drawings, wherein.

DETAILED DESCRIPTION

Figure 1:
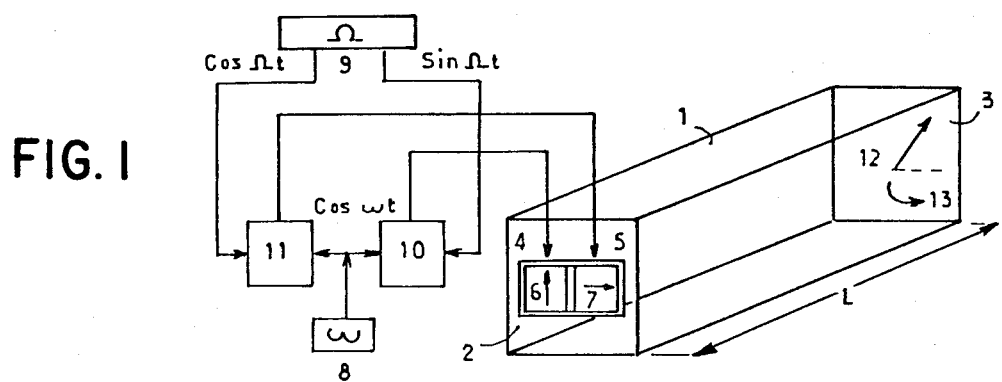
FIG. 1 shows an embodiment adapted to be used as a transmitter.
Figure 4:
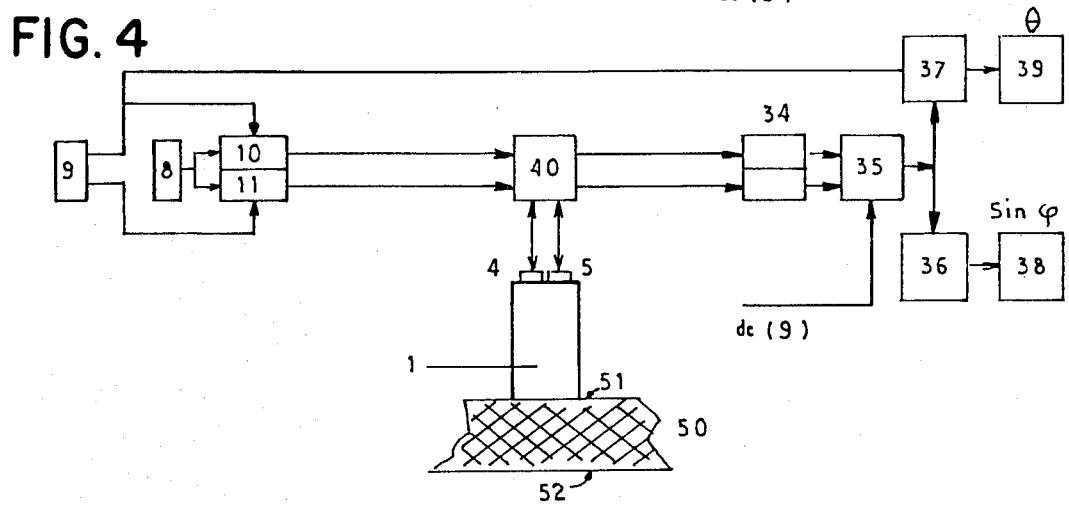
FIG. 4 shows an embodiment for the same purpose as in FIG. 3 but wherein the generated acoustic wave is reflected back through the structure to the same transducers which generated the wave.
Figure 5:
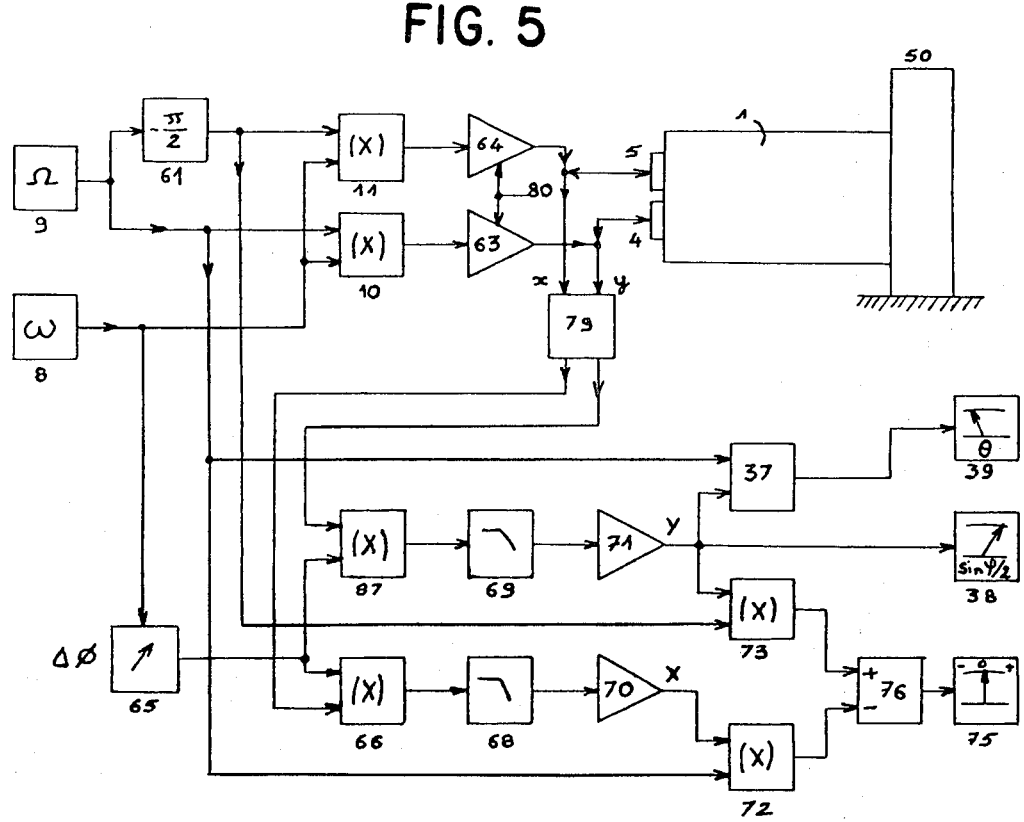
FIG. 5 shows a more detailed embodiment according to the general scheme of FIG. 4 and, FIG. 6 shows a partial modification of the device of FIG. 5.

First referring to FIG. 1, 1 is a body of elongated shape made of an isotropic material having fair properties of propagation of the transversal acoustic waves, especially at the higher frequencies of this wave-band. On one end face of said body 1, i.e. the end face 2, are applied two thin slabs 4 and 5 of a piezoelectric ceramic mateial o other suitable mateial to act as acoustic wave transducers having crossed axes of polarization as indicated by the two arrows 6 and 7. The slabs are for instance glued to the end face 2. FIG. 1, 4 and 5 show transmitters for acoustic waves, in the ultrasonic range. The isotropic material of the body 1 may be selected mainly from the group constituted by the alloyed steels and the aluminum alloys, the INVAR metal or any other material having good properties for propagating transversal acoustic waves of a basic frequency, for instance and illustratively of the order of the megahertz.

The transducers 4 and 5 are driven by voltages of said basic frequency, supplied by a generator 8 of a pulsation $\delta$, which are modulated by a low frequency oscillation of a pulsation $\Omega$, by 50 to 60 hertz for instance, generated by a generator 9 having two outputs, on in sin $\Omega t$ and the other one in cos$\Omega t$, so that the modulated voltages applied to the transducers are in relative phase quadrature. The cos$\Omega t$ voltage from 8 is modulated in circuits 10 and 11 respectively so that the transducer 4 receives the voltage $K.\sin\Omega t.\cos\omega t$ from the output of 10 and the transducer 5 receives the voltage $K.\cos\Omega\lambda t,\cos\omega t$ from the output of 11. K is a transfer constant.

The length L of the body 1 between its end faces, 2 for its drive and 3 for the emission of an acoustical wave, is made such that the two transversal waves applied by the transducers 4 and 5 can vectorially combine during their travel within the body. As the material of the body 1 is isotropic, the face 3 is excited to emit a resulting wave which is linear, of constant amplitude and rotates according to the arrow 13 at the speed $\Omega$, pulsation of the low frequency oscillation from 9.

Figure 2:
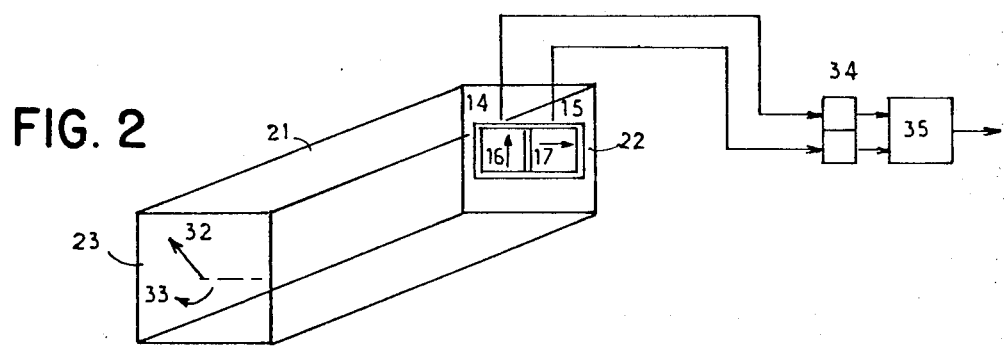
FIG. 2 shows an embodiment adapted to be used as a receiver.

The device may be made as a receiver, FIG. 2 wherein the elongated isotropic body 21 is of identical characteristics as the body 1 of FIG. 1, as the transducers 14 and 15 applied on an end face 22 of the body 21 are of identical characteristics as the transducers 4 and 5 of FIG. 1. The transducers 14 and 15 have their axes of polarization shown at 16 and 17. The body 21 receives on its end face 23 an acoustical wave, which is shown at 32 as undisturbed whereas it must be understood as being of elliptical non linear polarization and rotating in the direction of the arrow 33. The components of the applied waveform are, at the other end face, converted by the transducers into a pair of electrical voltages of the same forms as described for the emission. One component is in $\sin\Omega t.\cos\omega t$ and the other one is in $\cos\Omega t.\cos\omega t$ but of distinct amplitudes and phases. Such component voltages are amplified at 34 and applied therefrom to a handling circuit 35 which derives the values of the parameters of ellipticity of the input wave 32.

Figure 3:
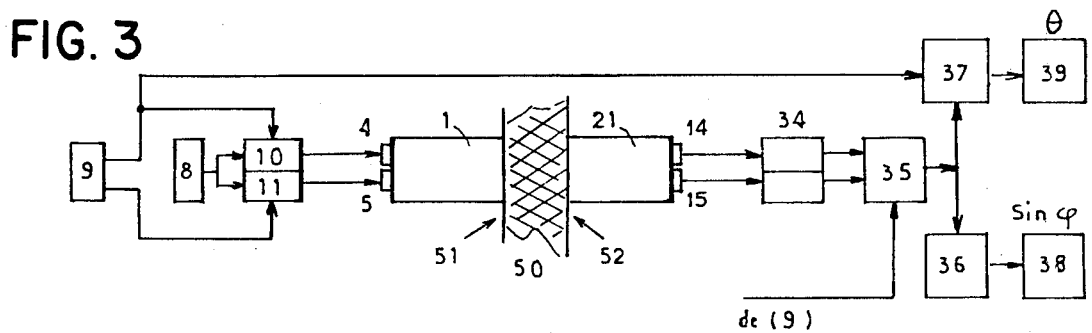
FIG. 3 shows an example of a complete system for the study of the anisotropy of a structure through which passes the acoustical wave generated by a device according to FIG. 1 from which issues a wave applied to a device according to FIG. 2.

The ellipticization of the linear acoustic wave may be the result of the application of wave issuing from the body 1 of FIG. 1 to a medium which presents an elastical (acoustical) anisotropy and such an elliptized acoustic wave is then collected when outputting from such a medium, 50 in FIGS. 3, 4 and 5. Said medium may present either an intrinsically anisotropic, material or substance or it may be a structure, which can be described as a "sample", wherein such anisotropy is created by application to the sample of a stress directed along an orientation $\theta$ in a plane which is perpendicular to the overall direction of propagation of the acoustic waves. Under such conditions, the sample 50 acts as a birefringent body having a slow axis parallel to the orientation of the stress and having a fast axis perpendicualr to said orientation. The acoustic waves which are applied are respectively polarized parallelarly to the said axes and consequently they present, at their output from 50, a phase difference $\phi$ of a value proportional to the value of the stress. For avoiding the creation of stationary waves in the device, the transducers 4 and 5 are fed with the above defined voltages after such voltages are pulsed as it will be herein under defined.

The circuit 35 which receives the waves outputting from the sample 50 may, for instance, handle as follows the two voltages amplified at 34, FIG. 3 and 4. These two voltages are respectively multiplied by $\cos\Omega t$ and $\sin\Omega t$. Difference is made between the two composition product voltages generated by such multiplications. The difference voltage is detected and filtered, resulting in a sine wave voltage the amplitude of which is measured at 36 and indicated at 38. This value is proportional in $\sin\phi$, which is a function of the intensity of the stress applied to the sample. The phase of said voltage, of a frequency $(\Omega t-\theta)$ is compared in the phasemeter 37 to the phase of the oscillation issued from 9 and the indicator 39 measures a voltage which is proportional to $\theta$, orientation of the stress.

The embodiment of FIG. 3 concerns the case when both faces of the sample 50 are available so that the acoustic waves can pass directly through it. On one side of the sample is appled the device of FIG. 1, on the opposite side of the sample is applied the device of FIG. 2.

The embodiment of FIG. 4 concerns the case when only one face of the sample is available. The acoustic waves enter the sample by the available face, are reflected back to the said face and collected for measurement of the amplitude and phase shift value due to the stress.

Only one pair of transducers 4 and 5 are then useful and a transmitter-receiver switch 40 ensures the switching of their functions from transmission to reception and back, as conventional per se.

One of the main advantages of a device according to the invention lies in the fact that the high and the low frequency oscillations each can have its frequency varied in a somewhat broad range of values without any necessity of simultaneously modifying the length L of the isotrope body 1 (respectively 21). The length L must be several times the wavelength of the high frequency oscillation, roughly from about 50 to about one hundred times said wavelength.

FIG. 5 shows a device illustrated in the same case as FIG. 4 though it must be plainly used in such as case as FIG. 3, showing an improved circuit arrangement for handling the signals outputting from the sample and received by the transducers acting as receivers for this purpose.

The transducers 4 and 5 are first activated for generating the acoustic waves which are sent through the isotrope body 1 to the sample 50 wherein they travel to and fro, pass anew through 1 and are received on the same transducers 4 and 5. As the voltages applied to the transducers are pulsed, a transmitter-receiver switch 79 suffices in the connections from 4 and 5 to the signal handling circuit arrangement for separating the transmitter side from the receiver side of the device. This switch is conventional as, as of common knowledge only connects the receiver arrangement to the receiver transducers after a time interval from the emission of the acoustic waves in the body 1 and sample 50, up to the next activation of the transducers for transmitting the waves. The time interval during which the switch 79 is blocked is a function of the average length of the acoustical path from the back to the transducers.

Two multiply circuits 10 and 11 ensure the modulation by two low frequency sine wave voltages from the generator 9, one being $\sin\Omega t$ and the other one $\cos\Omega t$ (the latter obtained by a dephaser circuit 61 adjusted to $\pi/2$), of the high frequency voltage from the generator 8. The $\sin\Omega t.\cos\omega t$ voltage is applied to the transducer 4 through an amplifier 63 to which is applied a chopping control voltage 80. The $\cos\Omega t.\cos\omega t$ voltage is similarly applied to the transducer 5 theough a chopper-amplifier circuit 64 controlled by the same chopper voltage 80. The pulsed acoustic wave combining the two pulsed transversal waves from the transducers at the output of the isotropic body 1 is applied to he sample 50, travels through it, is reflected back by the rear face and passes back through 1 to the transducers 4 and 5. Through 79, the two collected signals x of the $\sin\Omega t$ phase and y of the $\cos\Omega t$ phase, are available for deriving therefrom the values of the ellipticity parameters of the received wave and consequently values which measure the orientation and intensity of the stress applied to the sample 50.

The signals x and y are first multiples in 66 and 67 by a high frequency component derived from 8 through a phase-shifter circuit 65. The phase can be adjusted from 0° to 36° in this circuit. $\Delta\phi$ denotes the phase shift of the circuit which is manually adjustable. The composition product output voltages from 66 and 67 are respectively filtered by two-pass filters 68 and 69 so adjusted that only the components of the frequency $\Omega$ are preserved in said product voltages. These components are amplified at 70 and 71 issuing respective voltages X and Y of the said low frequency $\Omega$.

The amplitude of the Y voltage is, for instance, measured on an indicator 38.

The X voltage is multiplied by the $\sin\Omega t$ voltage issued from the generator 9, in a multiplier circuit 72 which delivers a signal $X.\sin\Omega t$. A multiplier circuit 73 similaraly multiplies the Y voltage by the $\cos\Omega t$ voltage issuing from 61 and delivers a signal $Y\cos.\Omega t$. These signals are applied to a differential amplifier 76 the output of which is measured on an indicator 75.

The phaseshift $\Delta\phi$ is first adjusted to zero or left at any value it may have. Then, it is manually adjusted to a value $\phi_o$ for which the output signal of 76 reaches a zero value read on 75. The phaseshift $\Delta\phi$ is finally adjusted to a value ($\phi_0 + 90°$). With this adjustment, the value read on 38, i.e. the value of $\sin\phi/2$, which is a function of the intensity of the stress which produces the anisotropy in the sample 50, is the true one. The intensity of the stress is proportional to $\phi$, which is consequently measured.

The voltage is further applied to a phasemeter 37 to which is applied, as a phase reference, the $\sin\Omega t$ voltage from 9. The voltage read on 39 at the output of the phasemeter 37 is a measure of $\theta$, orientation of the stress which generates the anisotropy in the sample 50.

The same circuits are plainly applicable to the case of FIG. 3 wherein they are appended to the transducers 14 and 15 delivering the x and y signals. No switch such as 79 is necessary.

Figure 6:
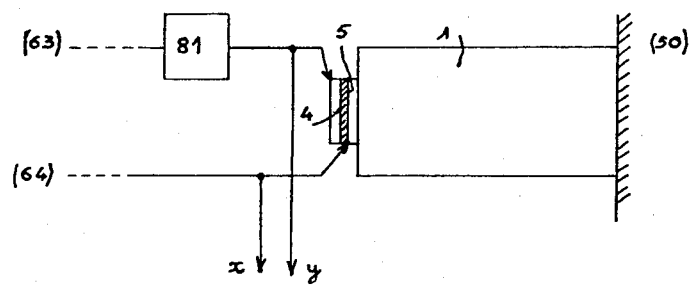

When, instead of placing the transducers side by side on the end face of the isotropic body 1, it is desired to stack them one over another on said face, as shown in FIG. 6, with a thin insulating film between them, a film of glue for instance, a slight phase displacement will apppear between the two acoustic waves generated in the isotropic body 1 by the transducers. The wave generated by the "outer" transducer will slightly lag with respect to the wave generated by the "inner" transducer. The waves must be either in phase or in phase opposition. Consequently, at least one phase adjustment circuit, such as the one shown at 81 in FIG. 6 must be provided. Said circuit could as well be provided in the link to the other transducer or, else, two such adjuster circuits can be provided, one in each link to the transducers from the chopper-amplifiers 63 and 64.

What is claimed is:

1. A transversal acoustic wave device for measuring anisotropy in an acoustically active substance of medium comprising:
    an elongated body of isotropic material having parallel end faces;
    a pair of transducers positioned on one only of said end faces, for launching acoustic waves in said body or for converting acoustic waves otherwise introduced into said body into electrical signals;
    said body being of sufficient length that when said transducers are driven by a pair of signals of ultrasonic frequency modulated by low frequency in quadrature phase relation, the acoustic signals in said body can vectorially combine to form a constant amplitude wave rotating at the speed of the modulating frequency.

2. A device as defined by claim 1 in which the isotropic material of said body is slected from the group consisting of aluminum alloys and steel alloys.

3. A device as defined by claim 1 in which the length of said body is between about 50 and 100 times the wavelength of the ultrasonic frequency to be fed to said transducers.

4. A device as defined by claim 3 for launching acoustic waves into said body and including: means for generating an ultrasonic electrical signal; means for generating sine and cosine low frequency signals; means for modulating said ultrasonic signal with said low frequency signals; and means coupling said modulated signals to said transducers.

5. A device as defined by claim 3 for receiving ellipticized acoustic waves applied to the end face of said body opposite said transducers and including a handling circuit connected to said transducers for coverting the outputs of said transducers into a sine wave for measuring the amplitude of phase shift thereof with respect to a reference sine wave to determine the parameters fo the ellipticized acoustic wave.

6. A device as defined by claim 3 for use as an emitter-receiver and including means for driving said transducers with ultrasonic low frequency modulated quadrature signals, means for converting the electrical output of said transducers to sine waves and means for connecting said device to function alternately in either emitting or receiving mode.

7. A device as defined by claim 4 including chopper amplfiers connected to drive said transducers.

8. A device as defined by claim 5 in which said handling circuit comprises:
    means forming the products of composition of the received signals and of a voltage derived from the high frequency wave oscillation of the transmitted signals;
    means extracting from the said products components of the low frequency oscillation of the transmitted signals;
    means measuring the amplitude and phase of one at least of the said components; and
    means for adjsting the conditions of validity of such measuring means.

9. A device as defined by claim 8 wherein said validity condition adjusting means comprises:
    means multiplying said low frequency components by the corresponding phase components of the low frequency oscillation;
    means forming the amplitude differences of the outputs of said multiplier means; and
    means adjusting the phase of the voltage derived from the high frequency wave oscillation up to first zeroing the output of said amplitude difference and secondly increasing the phase value adjustment by 90 degrees.

10. A device as defined by claim 8 wherein said phase adjusting means comprises a circuit adjustable from 0 degrees to 360 degrees connected to the output of said high frequency oscillation generator and said low frequency component extraction means comprises low-pass filters connected to the output of said composition product forming means and said product forming means being multiplier circuits.

11. A device as defined by claim 1 wherein one of said transducers overlies the other on said end face of said body and an adjustable phase shift control means is inserted in the drive of one of said transducers.

* * * * *